United States Patent
Wiegert et al.

(10) Patent No.: US 10,932,730 B2
(45) Date of Patent: Mar. 2, 2021

(54) METHOD FOR ESTIMATING THE RADIATION DOSE RECEIVED BY AN ORGAN DURING A COMPUTED TOMOGRAPHY SCAN

(71) Applicant: KONINKLIJKE PHILIPS N.V., Eindhoven (NL)

(72) Inventors: Jens Wiegert, Aachen (DE); Bernd Menser, Hauset (BE); Peter Prinsen, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 162 days.

(21) Appl. No.: 16/062,150

(22) PCT Filed: Dec. 16, 2016

(86) PCT No.: PCT/EP2016/081621
§ 371 (c)(1),
(2) Date: Jun. 14, 2018

(87) PCT Pub. No.: WO2017/103238
PCT Pub. Date: Jun. 22, 2017

(65) Prior Publication Data
US 2018/0368785 A1    Dec. 27, 2018

(30) Foreign Application Priority Data

Dec. 17, 2015   (EP) ..................................... 15200933

(51) Int. Cl.
*G06K 9/00*       (2006.01)
*A61B 6/03*       (2006.01)
(Continued)

(52) U.S. Cl.
CPC .............. *A61B 6/032* (2013.01); *A61B 6/488* (2013.01); *A61B 6/5223* (2013.01); *A61B 6/544* (2013.01);
(Continued)

(58) Field of Classification Search
CPC ......... A61B 6/488; A61B 6/032; A61B 6/463; A61B 6/5205; A61B 6/5223; A61B 6/544; G06T 7/0012
See application file for complete search history.

(56) References Cited

U.S. PATENT DOCUMENTS

| 5,418,715 A | 5/1995 | Deasy |
| 5,661,773 A | 8/1997 | Swerdloff |

(Continued)

FOREIGN PATENT DOCUMENTS

| JP | H04317665 | 11/1992 |
| JP | 2005143759 | 6/2005 |

(Continued)

OTHER PUBLICATIONS

Schlattl, et al., "Paper; Dose conversion coefficients for paediatric CT examinations with automatic tube current modulation"; Physics in Medicine and Biology; vol. 57, No. 20, Sep. 19, 2012.

*Primary Examiner* — Tom Y Lu
(74) *Attorney, Agent, or Firm* — Larry Liberchuk

(57) ABSTRACT

Method for estimating radiation dose received by a tissue of interest during an imaging scan comprising: i, obtaining image data of a body region including the tissue of interest, ii. sub-dividing the image data into axial slices, comprising tissue axial slices and non-tissue axial slices, iii. determining a net amount of radiation dose emitted or received by each axial slice by combining scan parameters of each axial slice (Continued)

with pre-calculated amounts of radiation dose, iiii summing the net amounts of radiation dose of all the tissue axial slices to obtain a tissue dose.

17 Claims, 3 Drawing Sheets

(51) Int. Cl.
    *A61B 6/00*     (2006.01)
    *G06T 7/00*     (2017.01)

(52) U.S. Cl.
    CPC ............ *G06T 7/0012* (2013.01); *A61B 6/463* (2013.01); *A61B 6/5205* (2013.01)

(56) References Cited

U.S. PATENT DOCUMENTS

| | | | |
|---|---|---|---|
| 7,787,669 B2 | 8/2010 | Botterweck | |
| 8,712,121 B2* | 4/2014 | Wiegert | ............. A61B 6/032 378/4 |
| 8,958,617 B2 | 2/2015 | Couch | |
| 9,140,803 B2* | 9/2015 | Bertram | ............. A61B 6/032 |
| 9,295,443 B2* | 3/2016 | Isola | ............. A61B 6/032 |
| 2004/0086076 A1 | 5/2004 | Nagaoka | |
| 2004/0131141 A1 | 7/2004 | Horiuchi | |
| 2009/0098856 A1 | 4/2009 | Hsu | |
| 2012/0148131 A1 | 6/2012 | Couch | |
| 2012/0148132 A1 | 6/2012 | Couch | |
| 2012/0150505 A1 | 6/2012 | Couch | |
| 2013/0156149 A1 | 6/2013 | Kohara | |
| 2014/0270053 A1 | 9/2014 | Larson | |
| 2015/0265224 A1 | 9/2015 | Gerland | |

FOREIGN PATENT DOCUMENTS

| | | |
|---|---|---|
| JP | 2010022692 | 2/2010 |
| JP | 2010269048 | 12/2010 |
| JP | 2013192750 | 9/2013 |
| WO | 2004067091 | 8/2004 |
| WO | 2012075577 | 6/2012 |
| WO | 2014/173851 | 10/2014 |

* cited by examiner

METHOD FOR ESTIMATING THE RADIATION DOSE RECEIVED BY AN ORGAN DURING A COMPUTED TOMOGRAPHY SCAN

CROSS REFERENCE TO RELATED APPLICATIONS

This application is the U.S. National Phase application under 35 U.S.C. § 371 of International Application No. PCT/EP2016/081621, filed Dec. 16, 2016, published as WO 2017/103238 on Jun. 22, 2017, which claims the benefit of European Patent Application Number 15200933.8 filed Dec. 17, 2015. These applications are hereby incorporated by reference herein.

The invention relates for estimating radiation dose. It also relates to a Computed Tomography device and to a computer readable storage medium.

BACKGROUND

Dose reporting in both Computed Tomography and conventional X-ray is becoming more and more important. In Computed Tomography it is possible to retrospectively calculate an absorbed radiation dose quite accurately from three-dimensional information about the tissue distribution in the CT scan from the patient. Such method is performed in US2009/0098856 for instance, in which fluence maps are constructed out of tomographic reconstruction algorithms applied to a full CT scan. However, although such a calculation gives access to an amount of radiation dose, it is implies performing a full scan hence it does not reduce the amount of radiation dose. Furthermore, such method gives no information about regions of the patient which were not scanned but received some scattered radiation nevertheless. Moreover, one needs accurate segmentation algorithms to calculate actual organ doses: these algorithms are quite accurate but are only useable when very precise conditions are met, and only in certain well studied organs. Such algorithms also assume that details of the scanner are available, whereas vendors are not always keen on providing these. Besides, due to slowness of the most accurate dose calculations, i.e. the Monte Carlo-based ones, in practice one always needs to resort to approximations. Finally, this approach makes use of a full three-dimensional volume, which limits possibilities of application, excluding notably all cloud based dose reporting systems or other environments with limited bandwidth or access to full image data.

In case of conventional X-ray the situation is even more complex since the only available data are derived from a projection of the patient, not a three-dimensional volume. Similar problems are met in CT when doing a prospective dose estimation based on a single scout image.

A method is described in US2012/0150505 to estimate the dose by choosing an adequate phantom scan in a library and then deforming it via interpolation in order to fit as well as possible the actual scan.

The present invention provides a solution to the problems met in prior art by providing an approximate dose calculation that is fast and relatively simple, circumvents the need to perform a full 3D dose calculation and organ segmentation, and does not require detailed knowledge of the scanner.

SUMMARY OF THE INVENTION

There is provided a method for estimating radiation dose received by a tissue of interest during an imaging scan which comprises obtaining image data of a body region including the tissue of interest, sub-dividing the image data into axial slices, comprising relevant axial slices and non-relevant axial slices, for each relevant axial slice, determining an amount of radiation dose received by combining scan parameters of each axial slice with pre-calculated amounts of radiation dose from each axial slice and summing the amounts of radiation dose of all the relevant axial slices to obtain a tissue dose.

The axis of the axial slices is preferably the body axis or an axis parallel to the body axis. As such, each slice receives a part of the X-Ray beam coming directly from the source, and a part of the X-Ray beam which is coming from other adjacent slices through scattering. Tissue-of-interest slices are slices which contain the tissue of interest, for instance, slices which contains at least a part of an organ of interest. A tissue slice may also be considered to be such only if the tissue of interest represents more than a certain fraction of the slice. Non-tissue slices are slices which are not tissue-of-interest slices.

The pre-calculated slice to slice dose propagation coefficients may be obtained from models taking into account local body parameters. Said pre-calculated coefficients may allow to eliminate the need for complicated contributions such as scattering and multi-scattering effects, which results in a simplified calculation of the net amount of radiation. In a preferred embodiment, the local body parameters characterize each slice combination to find a pair of slices with similar parameters in a database to retrieve a pre-calculated slice to slice dose propagation coefficient.

A quick estimation of dose after a scan, which is provided by the invention, may contain valuable information for technologists and doctors. Indeed, it may be used for education and possibly modification of protocols. It may also be valuable information to assess the probability of complications in patients at risk (e.g. with renal problems).

An advantage of the invention is that scan protocol and body anatomy are separated: only limited tabulation is required. Furthermore, details of the scanner are not required, which makes the calculation method vendor-independent and thus easy to apply. Finally, no access to the full CT dataset is required: this avoids data privacy issues.

In an aspect, the pre-calculated amounts of radiation dose are based on analysis of previously obtained radial dose information comprising a plurality of scans, preferably a plurality of scans stored in a database. This has the advantage that real-world data is being used.

The pre-calculated slice to slice dose propagation coefficients may also be obtained from models or simulations taking into account local body parameters. Said pre-calculated coefficients may allow to eliminate the need for complicated contributions such as scattering and multi-scattering effects, which results in a simplified calculation of the net amount of radiation. In a preferred embodiment, the local body parameters characterize each slice combination to find a pair of slices with similar parameters in a database to retrieve a pre-calculated slice to slice dose propagation coefficient.

A quick estimation of dose after a scan, which is provided by the invention, may contain valuable information for technologists and doctors. Indeed, it may be used for education and possibly modification of protocols. It may also be valuable information to assess the probability of complications in patients at risk (e.g. with renal problems).

An advantage of the invention is that scan protocol and body anatomy are separated: only limited tabulation is required. Furthermore, details of the scanner are not required, which makes the calculation method vendor-independent and thus easy to apply. Finally, no access to the full CT dataset is required: this avoids data privacy issues.

In an aspect the scan parameters comprise an intensity of activation.

In an aspect, the method further comprises a dose education and/or dose management step for a Computed Tomography imaging system and based on the tissue dose, preferably further comprising scan planning information based on the tissue dose.

In an each of the axial slices is classified as being either a dose-producing slice, a dose-transmitting slice or a dose-receiving slice.

In an aspect, at least one dose-producing slice is also a dose-receiving slice.

In an aspect, the method further comprising determining a water-equivalent diameter of each axial slice.

The water-equivalent diameter is a convenient parameter to characterize each slice. Said water-equivalent diameter may be determined based on information from a single scout scan. Said diameter may have an offset component, for instance in case the patient body is not in a centered position.

In an aspect the water-equivalent diameter is determined based on information from a single scout scan.

The method of the present invention is fast and has low bandwidth requirements as it can be made to work using only on a scout scan: this means it may also be used for analysis on databases containing a plurality of scans, e.g. in a service for hospitals to benchmark their dose usage.

In an aspect, adjustment coefficients are applied to the determined amount of radiation dose.

These may be used to adjust data which do not correspond to the exact scan parameters of the slice but which are close enough.

In an aspect, at least one of the axial slices corresponds with a Computed Tomography slice.

This may make the dose-calculation easier and allow easy retrieval of the data. However, the slicing may also be completely different.

In an aspect, the method further comprised determining a position-dependent Size Specific Dose Estimate of at least one axial slice.

In an aspect, Method according to any of the preceding claims further comprising: collecting statistics on dose usage.

There is also provided an imaging device configured to implement a method according to the above method and aspects thereof.

In an aspect, the imaging device is a radiation imaging device, such as an x-ray imaging device, preferably a computed tomography imaging device.

There is also provided a computer readable storage medium encoded with computer readable instructions, which, when executed by a processor, causes the processor to perform a method as described herein.

The method may also further comprise collecting statistics on dose usage. This is allows for feeding a database which potentially allows even faster data analysis or replacing missing dose usage with average expected amounts.

Still further aspects and embodiments of the present invention will be appreciated by those of ordinary skill in the art upon reading and understanding the following detailed description. Numerous additional advantages and benefits will become apparent to those of ordinary skill in the art upon reading the following detailed description of preferred embodiments.

BRIEF DESCRIPTION OF THE FIGURES

The invention shall be better understood by reading the following detailed description of an embodiment of the invention and by examining the annexed drawing, on which.

The invention may take form in various components and arrangements of components, and in various process operations and arrangements of process operations. The drawings are only for the purpose of illustrating preferred embodiments and are not to be construed as limiting the invention. To better visualize certain features may have been omitted or dimensions may not be according to scale.

DETAILED DESCRIPTION OF EMBODIMENTS

Figure 1:
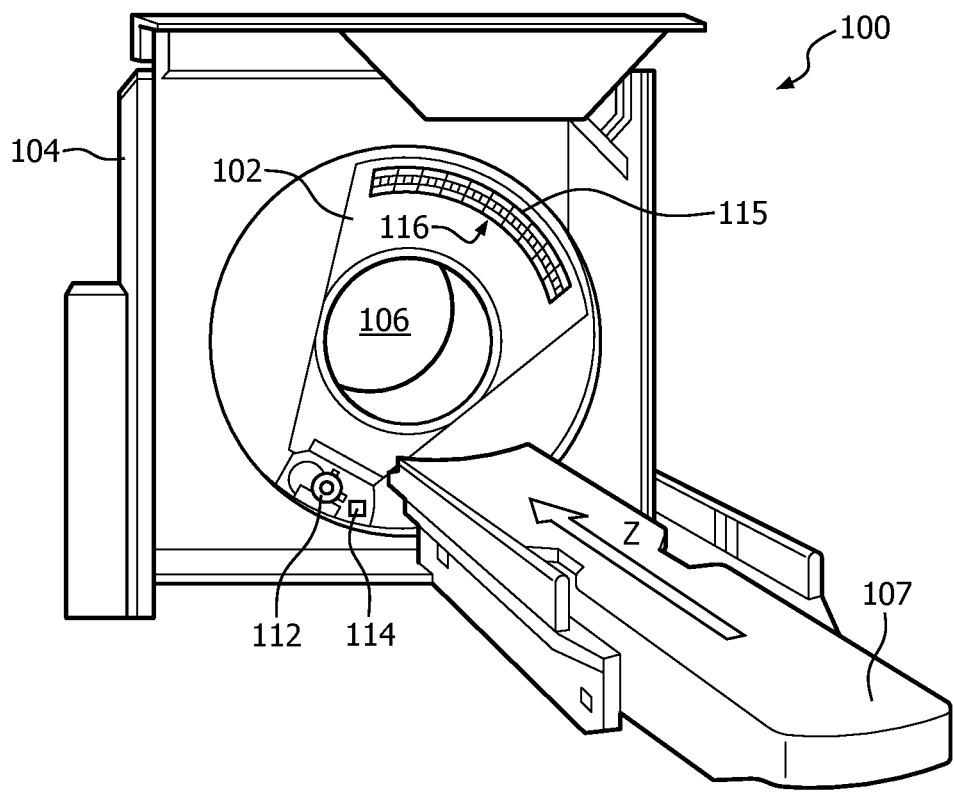
FIG. 1 shows a schematic depiction of a general Computed Tomography scanner.

FIG. 1 schematically illustrates an example imaging system 100; in this example a computed tomography (CT) scanner. The imaging system 100 includes a rotating gantry 102 and a stationary gantry 104. The rotating gantry 102 is rotatably supported by the stationary gantry 104. The rotating gantry 102 is configured to rotate around an examination region 106 about a longitudinal or z-axis. The imaging system 100 further includes a subject support 107 that supports a subject or object in the examination region 106 before, during and/or after scanning. The subject support 107 may also be used to load and/or unload the subject or object into or from the examination region 106. The imaging system 100 further includes a radiation source 112, such as an x-ray tube, that is rotatably supported by the rotating gantry 102. The radiation source 112 rotates with the rotating gantry 102 around the examination region 106 and is configured to generate and emit radiation that traverses the examination region 106. The imaging system 100 further includes a radiation source controller 114. The radiation source controller 114 is configured to modulate a flux of the generated radiation. For example, the radiation controller 114 may be configured to selectively change a cathode heating current of the radiation source 112, apply a charge to inhibit electron flow of the radiation source 112, filter the emitted radiation, etc. to modulate the flux. In the illustrated example, the radiation source controller 114 modulates the flux based on a predetermined modulation pattern.

The imaging system 100 further includes a one or two dimensional array 115 of radiation sensitive detector pixels 116. The pixels 116 are located opposite the radiation source 112, across the examination region 106, detect radiation traversing the examination region 106, and generate an electrical signal (projection data) indicative thereof. In the illustrated example, the pixels 116 include direct conversion photon counting detector pixels. With such pixels, the generated signal includes an electrical current or voltage having a peak amplitude or a peak height that is indicative of the energy of a detected photon. The direct conversion photon counting detector pixels may include any suitable direct conversion material such as CdTe, CdZnTe, Si, Ge, GaAs or other direct conversion material.

Figure 2:
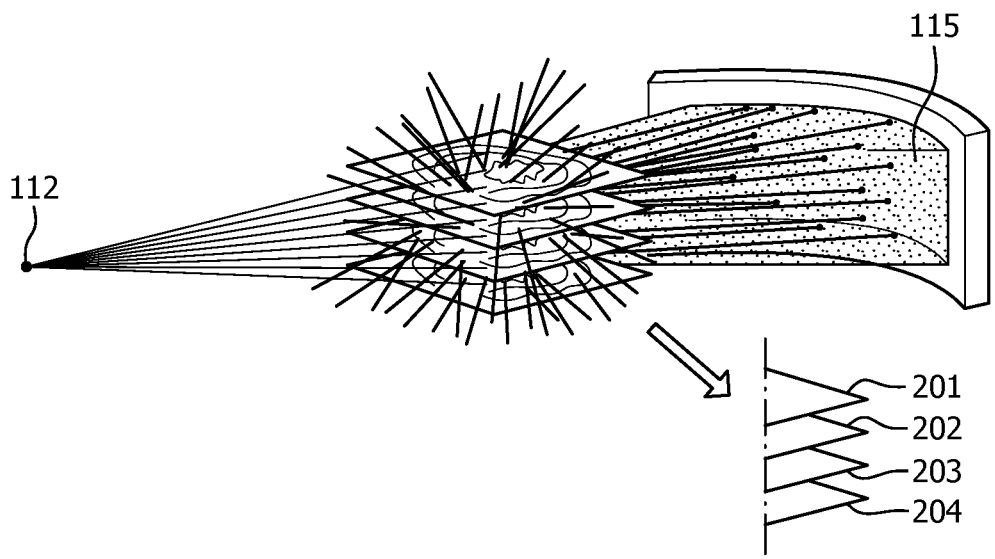
FIG. 2 schematically depicts different dose contributions of a slice of an imaged object.

When an object is imaged, part of the radiation is scattered. As such, the imaged object may receive radiation directly from the radiation source 112 but also indirectly, from surrounding tissues which are scattering part of the radiation it received. When the object is virtually divided into several slices 201, 202, 203, 204, as in FIG. 2, the total amount of radiation received by a slice 202 is the sum of the radiation directly received from the radiation source 112 and the radiation received from its adjacent slices 201, 203, 204 through scattering, and potentially also radiation received from scattered primary radiation in slice 202 itself. More specifically, a portion of the incident energy to each slice is absorbed within the slice, while another portion of the incident energy is scattered to other slices.

In a preferred embodiment described herein, pre-calculated slice to slice dose propagation coefficients provided by a database are used.

An imaged object, which may be either a patient or a phantom, is virtually divided up into axial slices. The slices which contain the tissue of interest will be referred to as tissue-of-interest slices or relevant slices. Each tissue-of-interest slice contains a certain fraction of the total tissue of interest. The total dose in a tissue of interest is calculated by summing up the dose contributions received by each tissue-of-interest slice, weighted by its corresponding tissue-of-interest fraction. To calculate the dose received by a tissue-of-interest, all slices are iteratively considered as dose-producing slices, one at a time (the remaining slices being considered as transmitting tissue). For each combination of dose-producing slice and dose-receiving slice (i.e. tissue-of-interest slice) the dose contribution is determined based on the characteristics of these two slices and those of the transmitting tissue in between. This assumes slices with similar characteristics in similar conditions will always scatter and multi-scatter radiation the same way.

Characteristics of a slice, determined e.g. from a scout image, in combination with consulting a database with pre-calculated results and selected scan parameters are used to determine how much dose/energy is 'generated' in a slice per unit activation, that is to say scattered toward the receiving slice instead of being absorbed/transmitted elsewhere. Similarly, dose deposition characteristics of the dose-receiving slice containing the organ of interest, determined e.g. from a scout image, in combination with look-up in a database with pre-calculated results are determined. Finally, characteristics of the intervening slices are determined in a similar way. These are then combined to calculate the dose deposition due to a dose-producing slice in a receiving slice. This calculation could also be done by means of a pre-calculated lookup table with associated parameters based on the characteristics described above. By weighting and summing all contributions one obtains the total dose in the tissue of interest.

The actual algorithm used in the present example is detailed below. First of all, a dose sensitive tissue of interest (e.g. an organ) is determined. For each dose-receiving slice within a dose sensitive tissue of interest (i.e. a tissue-of-interest slice), the algorithm considers iteratively every slice within the scan region as a 'dose-producing slice' and determines their intensity of activation according to the scan protocol. The intensity of activation $I_i$ is a measure for the amount of primary radiation received by slice i from the source. $D_{ij}$ is the dose per unit of activation that reaches the tissue-of-interest in slice j through scattering and attenuation processes in slice i and the slices between i and j. The values of $D_{ij}$ are retrieved in this example from a database using a series of query parameters. Examples of the query parameters may be things like water-equivalent diameter at location i, water-equivalent diameter at location j, average water-equivalent diameter in the slices between i and j, relative position of slice j with respect to all slices containing the same tissue of interest, position of the patient's arms (up or down), off-centering, and tube spectrum (kVp and filtering). The algorithm applies adjustment coefficients $m_{ij}$ in case query values do not correspond exactly to those available in the database. For example, an interpolation between retrieved values of $D_{ij}$ for query values on either side of the actual query value could be performed or a weighted average of the two retrieved values $D_{ij}$ could be calculated. Other methods are of course possible.

The retrieved values $D_{ij}$ are then used in the determination of the dose contributions of each slice in combination with the scan parameters of that slice. For example, the values $D_{ij}$ may be multiplied with a weight determined from the intensity of activation of each slice. By summing contributions, it is possible to obtain a quick estimate of the dose received by each slice.

The algorithm determines a tissue-of-interest weight $W_j$ for each dose receiving slice. A typical choice for $W_j$ is a value proportional to the mass of the tissue of interest in that particular slice. Another choice is the tissue-of-interest fraction in a slice.

Finally all contributions are summed and normalized by the sum of tissue-of-interest weights to obtain an estimate of the radiation dose D(tissue of interest) received by the whole dose-sensitive tissue of interest. The informal formula below illustrates this.

$$D(\text{tissue of interest}) = \frac{\sum_{j=1}^{R} W_j \left( \sum_{i=1}^{P} I_i m_{ij} D_{ij} \right)}{\sum_{j=1}^{R} W_j}$$

for R receiving slices j and P producing slices i.

The database may contain contributions from many hours of Monte Carlo simulations from which the model then may obtain the corresponding information in split seconds. By picking the right information in the database, the method allows to save a significant amount of time.

Depending on whether a slice is considered as a dose-producing slice, transmitting slice, or dose-receiving slice, the parameters used to characterize each slice are different.

The pre-calculated slice to slice dose propagation coefficients may be obtained from models or simulations taking into account local body parameters. Said pre-calculated coefficients may allow to eliminate the need for complicated contributions such as scattering and multi-scattering effects, which results in a simplified calculation of the net amount of radiation. In a preferred embodiment, the local body parameters characterize each slice combination to find a pair of slices with similar parameters in a database to retrieve a pre-calculated slice to slice dose propagation coefficient.

Figure 3:
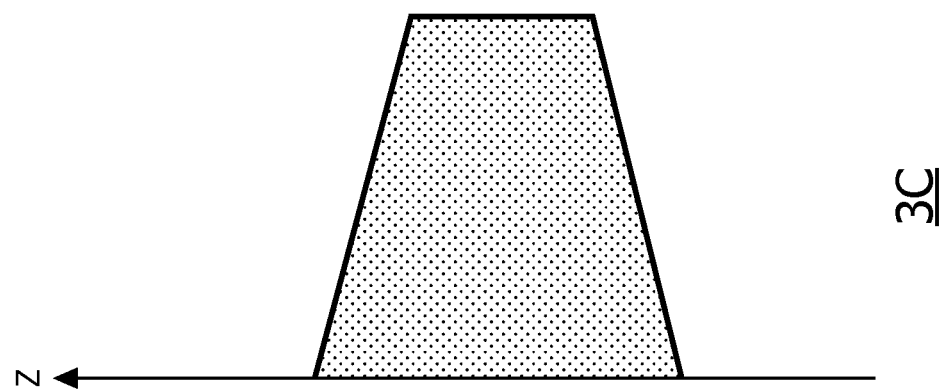
FIG. 3 shows an example of modeling of intensity of activation in a dose-producing slice.
Figure 3:
Figure 3:
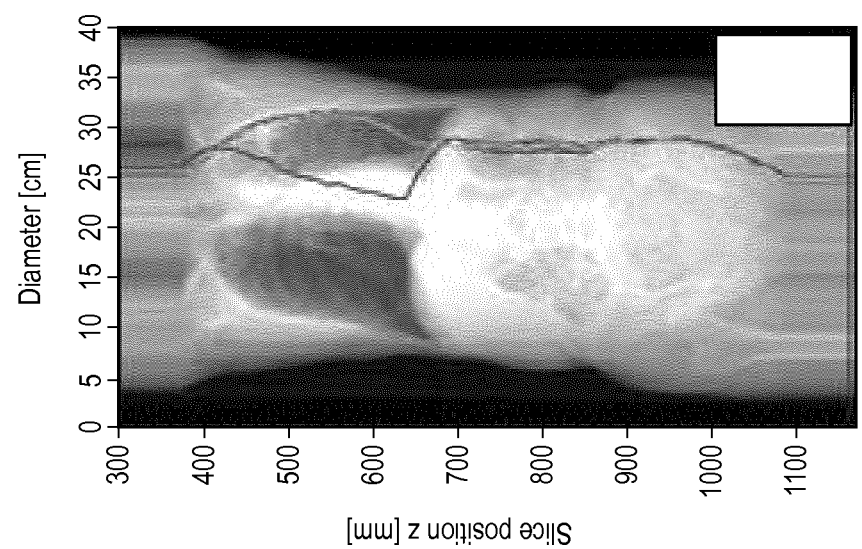

FIG. 3 shows the estimated intensity of activation of each slice. FIG. 3A shows image data obtained from a scout Computed Tomography scan and FIG. 3B show the corresponding intensity of activation.

Here, the purpose is to separate scan protocol from object properties (the imaged patient or phantom).

This is done by mapping the impact of the scan protocol to an "activation profile of dose-producing slices" as plotted in 3B. A person skilled in the art may find a plethora of ways to express such mappings and the ones shown here are only options for potential embodiments.

A Computed Tomography detector is irradiated with an appropriately collimated radiation cone characterized by its beam shaper profile and a collimation width. Tube current may be modulated while the tube exhibits a helical or axial trajectory around the patient.

The simplest way to express the activation of a slice is by using the tube current integral of I(t)*dt, integrated over the time the focal spot needs to cross the defined extent of the chosen slice in the body axis z direction. In the foregoing, I(t) is the tube current and dt is an infinitesimal increment of time.

In a more refined way one can take into account the cone beam nature of the beam by convolving the above expression with a trapezoidal opening approximating the primary flux contribution of the cone beam given a local tube position, as roughly pictured in FIG. 3C.

Figure 4:
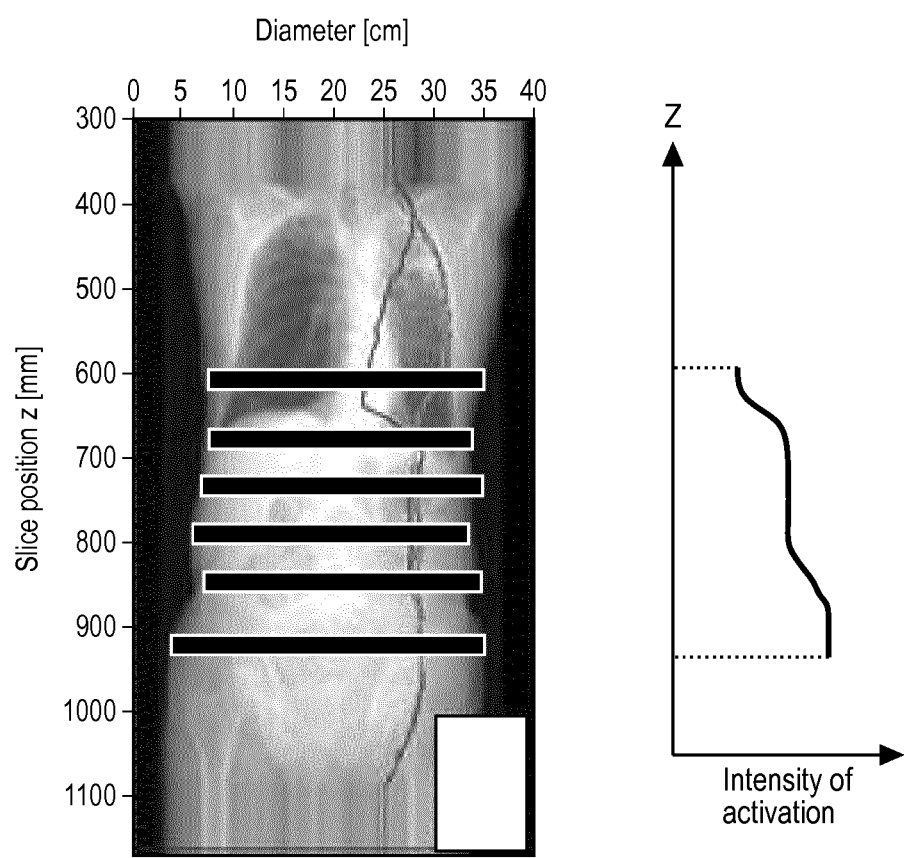
FIG. 4 shows an example of modeling of a series of parameters in a dose-producing slice.

Once the intensity profile has been determined, it is possible to characterize each slice with a set of chosen parameters, as in FIG. 4. The person skilled in the art may again define many ways how to do this. Preferably, at least one parameter will be intensity related, for instance, one parameter may be the actual intensity of activation.

A number of further parameters will be used later for database lookup and potential adjustment to lookup position. In the exemplified embodiment, the parameters are water-equivalent diameter, position on the z-reference scale, position of the patient's arms (up or down), off-centering, and tube spectrum (kVp and filtering).

Thus the method for estimating radiation dose received by a tissue of interest during an imaging scan comprises obtaining image data of a body region including the tissue of interest, sub-dividing the image data into axial slices, comprising relevant axial slices and non-relevant axial slices, for each relevant axial slice, determining an amount of radiation dose received by combining scan parameters of each axial slice with pre-calculated amounts of radiation dose from each axial slice and summing the amounts of radiation dose of all the relevant axial slices to obtain a tissue dose.

The axis of the axial slices is preferably the body axis or an axis parallel to the body axis. As such, each slice receives a part of the X-Ray beam coming directly from the source, and a part of the X-Ray beam which is coming from other adjacent slices through scattering. Tissue-of-interest slices are slices which contain the tissue of interest, for instance, slices which contains at least a part of an organ of interest. A tissue slice may also be considered to be such only if the tissue of interest represents more than a certain fraction of the slice. Non-tissue slices are slices which are not tissue-of-interest slices.

The pre-calculated slice to slice dose propagation coefficients may be obtained from models taking into account local body parameters. Said pre-calculated coefficients may allow to eliminate the need for complicated contributions such as scattering and multi-scattering effects, which results in a simplified calculation of the net amount of radiation. In a preferred embodiment, the local body parameters characterize each slice combination to find a pair of slices with similar parameters in a database to retrieve a pre-calculated slice to slice dose propagation coefficient.

A quick estimation of dose after a scan, which is provided by the invention, may contain valuable information for technologists and doctors. Indeed, it may be used for education and possibly modification of protocols. It may also be valuable information to assess the probability of complications in patients at risk (e.g. with renal problems).

An advantage of the invention is that scan protocol and body anatomy are separated: only limited tabulation is required. Furthermore, details of the scanner are not required, which makes the calculation method vendor-independent and thus easy to apply. Finally, no access to the full CT dataset is required: this avoids data privacy issues.

FIG. 4 shows an example with different centering positions as well as indicated intensities of activation.

The dose-receiving organ in the dose-receiving slice and the transmitting tissue are again modeled by a number of parameters. The person skilled in the art may again define many ways how to do this. In the present example, the dose-receiving slices are characterized by the organ type, its relative position within an organ of interest, its water-equivalent diameter, and a body offset; and the transmitting tissue is characterized by its average radiological path length and its average water-equivalent diameter.

The water-equivalent diameter is determined based on information from a single scout scan. This method can be fast and have low bandwidth requirements as it can be made to work using only on a scout scan: this means it may also be used for analysis on databases containing a plurality of scans, e.g. in a service for hospitals to benchmark their dose usage.

While the invention has been illustrated and described in detail in the drawings and foregoing description, such illustration and description are to be considered illustrative or exemplary and not restrictive; the invention is not limited to the discussed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

The invention claimed is:

1. A method for estimating a radiation dose received by a tissue of interest during an imaging scan, comprising:
   obtaining a scout image of a body region including the tissue of interest;
   sub-dividing image data from the scout image into axial slices, comprising relevant axial slices and non-relevant axial slices, the relevant axial slices being the slices comprising a fraction of a total of the tissue of interest;
   for each dose receiving relevant axial slice, determining an amount of the radiation dose received, by iteratively calculating for each axial slice the contributed amount of radiation dose, combining scan parameters of the axial slice with pre-calculated amounts of the radiation dose from the axial slice,
   wherein the scan parameters comprise an intensity of activation, and the pre-calculated amounts of the radiation dose are determined by retrieving from a database a dose per unit of activation that reaches the dose receiving relevant axial slice through scattering and attenuation processes in the axial slice and the slices between the dose receiving relevant axial slice and each axial slice; and
   summing the amounts of the radiation dose of all the dose receiving relevant axial slices to obtain a tissue dose by applying a formula $$D(\text{tissue of interest}) = \frac{\sum_{j=1}^{R} W_j \left( \sum_{i=1}^{P} I_i m_{ij} D_{ij} \right)}{\sum_{j=1}^{R} W_j}$$

for R dose receiving relevant axial slices (j) and P producing each axial slice (i), wherein $W_j$ is a tissue of interest weight for each dose receiving slice (j), $I_i$ is the intensity of activation, $m_{ij}$ is an adjustment coefficient, and $D_{ij}$ is the dose per unit of activation.

2. The method according to claim 1, wherein the pre-calculated amounts of the radiation dose are based on analysis of previously obtained radiation dose information comprising a plurality of scans.

3. The method according to claim 1, further comprising a dose education and/or dose management for a Computed Tomography imaging system and based on the tissue dose.

4. The method according to claim 1, wherein each of the axial slices is classified as being either a dose-producing slice, a dose-transmitting slice or a dose-receiving slice.

5. The method according to claim 1, wherein at least one dose-producing slice is also a dose-receiving slice.

6. The method according to claim 1, further comprising: determining a water-equivalent diameter of each axial slice.

7. The method according to claim 6, wherein the water-equivalent diameter is determined based on information from a single scout scan.

8. The method according to claim 1, wherein adjustment coefficients are applied to the determined amount of radiation dose.

9. The method according to claim 1, wherein at least one of the axial slices corresponds with a Computed Tomography slice.

10. The method according to claim 1, further comprising: determining a position-dependent Size Specific Dose Estimate of at least one axial slice.

11. The method according to claim 1, further comprising: collecting statistics on dose usage.

12. The method according to claim 1, wherein the radiation dose received by the tissue of interest during an imaging scan is estimated.

13. The method according to claim 2, wherein the plurality of scans is stored in a database.

14. The method according to claim 3, further comprising scan planning information based on the tissue dose.

15. An imaging device configured to implement a method for estimating a radiation dose received by a tissue of interest during an imaging scan, comprising:
  obtaining a scout image of a body region including the tissue of interest;
  sub-dividing image data from the scout image into axial slices, comprising relevant axial slices and non-relevant axial slices, the relevant axial slices being the slices comprising a fraction of a total of the tissue of interest;
  for each dose receiving relevant axial slice, determining an amount of the radiation dose received, by iteratively calculating for each axial slice the contributed amount of radiation dose, combining scan parameters of the axial slice with pre-calculated amounts of the radiation dose from the axial slice,
  calculated amounts of the radiation dose are determined by retrieving from a database a dose per unit of activation that reaches the dose receiving relevant axial slice through scattering and attenuation processes in the axial slice and the slices between the dose receiving relevant axial slice and each axial slice; and
  wherein the scan parameters comprise an intensity of activation, and the pre-calculated amounts of the radiation dose are determined by retrieving from a database a dose per unit of activation that reaches the dose receiving relevant axial slice through scattering and attenuation processes in the axial slice and the slices between the dose receiving relevant axial slice and each axial slice; and
  summing the amounts of the radiation dose of all the dose receiving relevant axial slices to obtain a tissue dose by applying a formula $$D(\text{tissue of interest}) = \frac{\sum_{j=1}^{R} W_j \left( \sum_{i=1}^{P} I_i m_{ij} D_{ij} \right)}{\sum_{j=1}^{R} W_j}$$

for R dose receiving relevant axial slices (j) and P producing each axial slice (i), wherein $W_j$ is a tissue of interest weight for each dose receiving slice (j), $I_i$ is the intensity of activation, $m_{ij}$ is an adjustment coefficient, and $D_{ij}$ is the dose per unit of activation.

16. The imaging device according to claim 15, wherein the imaging device comprises an x-ray imaging device.

17. A non-transitory computer readable storage medium encoded with computer readable instructions, which, when executed by processor circuitry, causes the processor circuitry to perform a method for estimating a radiation dose received by a tissue of interest during an imaging scan, the method comprising:
  obtaining a scout image of a body region including a tissue of interest;
  sub-dividing image data from the scout image into axial slices, comprising relevant axial slices and non-relevant axial slices, the relevant axial slices being the slices comprising a fraction of a total of the tissue of interest;
  for each dose receiving relevant axial slice, determining an amount of the radiation dose received, by iteratively calculating for each axial slice the contributed amount of radiation dose, combining scan parameters of the axial slice with pre-calculated amounts of the radiation dose from the axial slice,
  wherein the scan parameters comprise an intensity of activation, and the pre-calculated amounts of the radiation dose is determined by retrieving from a database a dose per unit of activation that reaches the dose receiving relevant axial slice through scattering and attenuation processes in the axial slice and the slices between the dose receiving relevant axial slice and each axial slice; and
  summing the amounts of the radiation dose of all the dose receiving relevant axial slices to obtain a tissue dose by applying a formula $$D(\text{tissue of interest}) = \frac{\sum_{j=1}^{R} W_j \left( \sum_{i=1}^{P} I_i m_{ij} D_{ij} \right)}{\sum_{j=1}^{R} W_j} \quad \quad 5$$

for R dose receiving relevant axial slices (j) and P producing each axial slice (i), wherein $W_j$ is a tissue of interest weight for each dose receiving slice (j), $I_i$ is the intensity of activation, $m_{ij}$ is an adjustment coefficient, and $D_{ij}$ is the dose per unit of activation.

* * * * *